United States Patent
Busch-Petersen et al.

(10) Patent No.: US 7,384,946 B2
(45) Date of Patent: *Jun. 10, 2008

(54) M₃ MUSCARINIC ACETYLCHOLINE RECEPTOR ANTAGONISTS

(75) Inventors: Jakob Busch-Petersen, King of Prussia, PA (US); Anthony W. J. Cooper, Stevenage (GB); Dramane I. Laine, King of Prussia, PA (US); Brent W. McCleland, King of Prussia, PA (US); Michael R. Palovich, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 97 days.

This patent is subject to a terminal disclaimer.

(21) Appl. No.: 10/598,882

(22) PCT Filed: Mar. 17, 2004

(86) PCT No.: PCT/US2004/008027

§ 371 (c)(1),
(2), (4) Date: Sep. 14, 2006

(87) PCT Pub. No.: WO2005/095407

PCT Pub. Date: Oct. 13, 2005

(65) Prior Publication Data

US 2007/0149598 A1  Jun. 28, 2007

(51) Int. Cl.
*C07D 487/08* (2006.01)
*C07D 401/14* (2006.01)
*C07D 403/14* (2006.01)
*A61K 31/403* (2006.01)
*A61K 31/497* (2006.01)
*A61K 31/4439* (2006.01)

(52) U.S. Cl. .......... 514/255.05; 514/339; 514/411; 544/405; 546/276.7; 548/428

(58) Field of Classification Search ............ 544/405; 546/276.7; 548/428; 514/255.05, 339, 411
See application file for complete search history.

(56) References Cited

U.S. PATENT DOCUMENTS

| | | |
|---|---|---|
| 3,634,852 A | 1/1972 | Hartley et al. |
| 5,590,645 A | 1/1997 | Davies et al. |
| 5,860,419 A | 1/1999 | Davies et al. |
| 5,873,360 A | 2/1999 | Davies et al. |
| 6,455,527 B2 | 9/2002 | Tulshian et al. |
| 6,696,462 B2 | 2/2004 | Eickmeier et al. |
| 6,750,226 B2 | 6/2004 | Forner et al. |
| 7,232,841 B2 | 6/2007 | Busch-Petersen et al. |
| 7,276,521 B2 | 10/2007 | Busch-Petersen et al. |
| 2005/0277676 A1 | 12/2005 | Laine et al. |
| 2006/0160844 A1 | 7/2006 | Belmonte et al. |
| 2006/0178395 A1 | 8/2006 | Belmonte et al. |
| 2006/0178396 A1 | 8/2006 | Belmonte et al. |
| 2007/0129396 A1 | 6/2007 | Wan et al. |
| 2007/0135478 A1 | 6/2007 | Palovich et al. |
| 2007/0173646 A1 | 7/2007 | Laine et al. |
| 2007/0179180 A1 | 8/2007 | Busch-Petersen et al. |
| 2007/0179184 A1 | 8/2007 | Busch-Petersen et al. |
| 2007/0185088 A1 | 8/2007 | Busch-Petersen et al. |
| 2007/0185090 A1 | 8/2007 | Busch-Petersen et al. |
| 2007/0185148 A1 | 8/2007 | Busch-Petersen et al. |
| 2007/0185155 A1 | 8/2007 | Laine et al. |
| 2007/0232599 A1 | 10/2007 | Palovich et al. |
| 2007/0249664 A1 | 10/2007 | Laine et al. |

FOREIGN PATENT DOCUMENTS

| | | |
|---|---|---|
| EP | 0069715 | 6/1982 |
| GB | 2064336 | 6/1981 |
| GB | 2129691 | 5/1984 |
| GB | 2169265 | 7/1986 |
| GB | 2178965 | 2/1987 |
| GB | 2242134 | 9/1991 |
| WO | 87/05213 | 9/1987 |
| WO | 2006/050239 | 5/2006 |
| WO | 2006/055503 | 5/2006 |
| WO | 2006/055553 | 5/2006 |
| WO | 2006/062883 | 6/2006 |
| WO | 2006/062931 | 6/2006 |
| WO | 2006/065755 | 6/2006 |
| WO | 2006/065788 | 6/2006 |
| WO | 2007/016639 | 2/2007 |
| WO | 2007/016650 | 2/2007 |
| WO | 2007/018508 | 2/2007 |
| WO | 2007/018514 | 2/2007 |

(Continued)

OTHER PUBLICATIONS

Carcache et al., Helvetica Chimica Acta, 2003, 8696), 2192-2209.*
U.S. Appl. No. 10/585,830, filed Jul. 12, 2006, Laine, et al.
U.S. Appl. No. 10/598,743, filed Sep. 11, 2006, Budzik, et al.
U.S. Appl. No. 10/598,750, filed Sep. 11, 2006, Jin, et al.
U.S. Appl. No. 10/599,717, filed Oct. 6, 2006, Laine, et al.
U.S. Appl. No. 11/570,981, filed Dec. 20, 2006, Cooper, et al.
U.S. Appl. No. 11/573,097, filed Feb. 2, 2007, Busch-Petersen, et al.
U.S. Appl. No. 11/573,099, filed Feb. 2, 2007, Busch-Petersen, et al.
U.S. Appl. No. 11/766,318, filed Jun. 21, 2007, Busch-Petersen, et al.

(Continued)

*Primary Examiner*—Fiona T Powers
(74) *Attorney, Agent, or Firm*—Dara L. Dinner; Mary E. McCarthy; Charles M. Kinzig

(57) ABSTRACT

Novel dimeric benzoazabicyclohepatane compounds, pharmaceutical compositions, processes for their preparation and use thereof in treating M₃ muscarinic acetylcholine receptor mediated diseases are disclosed.

19 Claims, No Drawings

FOREIGN PATENT DOCUMENTS

WO 2007/022351 2/2007

OTHER PUBLICATIONS

U.S. Appl. No. 11/766,371, filed Jun. 21, 2007, Busch-Petersen, et al.
U.S. Appl. No. 11/774,885, filed May 1, 2006, Wan, et al.
Brown, *History and Basic Properties*, Humana Press, USA pp. 7-9 (1989).
Caulfield, *Pharmac. Ther.*, vol. 58 pp. 319-379 (1993).
Costello, et al., *American Journal of Physiology*, vol. 276 (5) pp. L709-L714 (1999).
Fryer and Jacoby, *Am J Respir Crit Care Med*, vol. 158 (5, pt 3) pp. 154-160 (1998).
Fryer et al., *Life Sci*, vol. 64 (6-7) pp. 449-455 (1999).
Hedge, et al., *Life Sciences*, vol. 64 (6/7) pp. 419-428 (1999).
Ikeda, et al., *Naunyn-Schmiedeberg's Arch Pharmacol.*, vol. 366, pp. 97-103, (2002).
Minette, et al., *Journal of Applied Physiology*, vol. 67(6) pp. 2461-2465 (1989).
Oprins, et al., *Annals of the New York Academy of Sciences*, vol. 915 pp. 102-106 (2000).
Pauwels et al., *Am. J. Respir. Crit. Care Med.*, vol. 163 pp. 1256-1276 (2001).
Ran, et al., *Yaoxue Xuebao*, vol. 19 (5) pp. 361-366 (1984) Abstract only.
Sarau, *Mol. Pharmacol.*, vol. 56 (3) p. 657-63 (1999).
Van Rossum, et al., *Arch. Int. Pharmacodyn.*, vol. 143 p. 299 (1963) Best Available Copy.
Wu, et al., *Zhongguo Yaowu Huazue Zazhi*, vol. 3 (1) pp. 23-26 (1993)Abstract only.
Zirkle, et al., *J Med Chem*, vol. 27 pp. 1269-1279 (1962).
Zirkle, et al., *J Med Chem*, vol. 27 pp. 1279-1285 (1962).
Zirkle, et al., *J Med Chem*, vol. 5 pp. 341-356 (1962).
Zhang, et al., *J Med Chem*, vol. 44 pp. 3937-3945 (2001).

\* cited by examiner

M₃ MUSCARINIC ACETYLCHOLINE RECEPTOR ANTAGONISTS

FIELD OF THE INVENTION

This invention relates to novel dimeric benzoazabicycloheptane compounds, pharmaceutical compositions, processes for their preparation, and use thereof in treating muscarinic acetylcholine receptor mediated diseases.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs, and these receptors can mediate both inhibitory and excitatory actions. For example, in smooth muscle found in the airways, bladder and gastrointestinal tract, mAChRs mediate contractile responses (1989. The Muscarinic Receptors. The Humana Press, Inc., Clifton, N.J.).

Muscarinic acetylcholine receptor dysfunction has been noted in a variety of different pathophysiological states. For instance, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation. This mAChR dysfunction results in airway hyperreactivity mediated by increased stimulation of mAChRs. Similarly, inflammation of the gastrointestinal tract in inflammatory bowel disease (IBD) results in mAChR-mediated hypermotility (Oprins, J. C. J., HP. Meijer, and J. A. Groot. 2000. Tumor Necrosis Factor-{alpha} Potentiates Ion Secretion Induced by Muscarinic Receptor Activation in the Human Intestinal Epithelial Cell Line HT29cl.19A. Ann NY Acad Sci 915:102-106). Incontinence due to bladder hypercontractility has also been demonstrated to be mediated through increased stimulation of mAChRs. Thus the identification of subtye-selective mAChR antagonists may be useful as therapeutics in these mAChR-mediated diseases.

Despite the large body of evidence supporting the use of anti-muscarinic receptor therapy for treatment of a variety of disease states, relatively few anti-muscarinic compounds are in use in the clinic. Thus, there remains a need for novel compounds that are capable of causing blockade at mAChRs. Conditions associated with an increase in stimulation of mAChRs, such as asthma, COPD, IBD and urinary incontinence would benefit by compounds that are inhibitors of mAChR binding.

SUMMARY OF THE INVENTION

This invention provides for a method of treating a muscarinic acetylcholine receptor (mAChR) mediated disease, wherein acetylcholine binds to an mAChR and which method comprises administering an effective amount of a compound of Formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

The present invention also provides for the novel compounds of Formula (I), and pharmaceutical compositions comprising a compound of Formula (I), and a pharmaceutical carrier or diluent.

Formula (I)

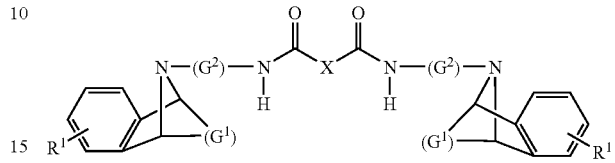

wherein:
$R^1$ is selected from the group consisting of hydrogen, halogen, $C_{1-4}$ alkyl, $C_{1-4}$ alkanoyl and aroyl;
$G^1$ represents $CH_2$—$CH_2$ or $CH$=$CH$;
$G^2$ represents $C_{4-7}$alkyl or a group of the formula (a), (b) or (c):

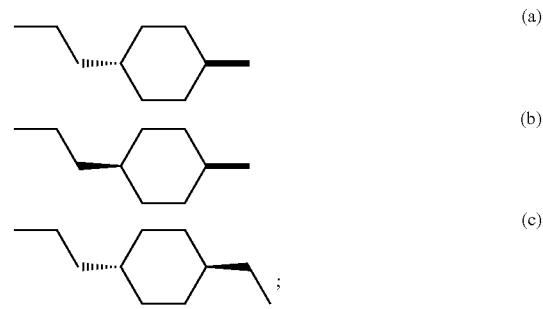

X represents a group of the formula (d), (e) or (f):

 (d)

 (e)

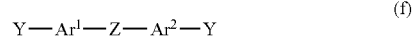 (f)

wherein
Y is, independently, selected from the group consisting of a bond, O, S, $NR^2$, —$NR^2$—$C_{1-4}$ alkyl-, and $C_{1-4}$ alkyl- each of these alkyl groups may contain a heteroatom selected from O, $NR^2$, or S;
$R^2$ is, independently, selected from the group consisting of a hydrogen, $C_{1-4}$ alkyl or $C_{1-4}$ alkyl-aryl;
Ar, $Ar^1$ and $Ar^2$ are, independently, selected from the group consisting of an optionally substituted phenyl rings, optionally substituted 5- or 6-membered aromatic heterocyclic rings or optionally substituted, fused bicyclic or tricyclic aromatic or heteroaromatic ring systems;
L is, independently, selected from the group consisting of a bond, optionally substituted $C_{1-4}$ alkanoyl, $C_{1-4}$ alkenyl, $C_{1-4}$ alkynyl or $C_{1-18}$ alkyl which may contain between 0 and 3 heteroatoms independently selected from O , $NR^2$, or S; also, atoms within L may be joined to form up to 3 rings and additionally, L may be have up to 3 aryl, heteroaryl or —$CO_2R^2$ substituents;

Z represents a bond, O, $NR^2$, S, $C_{1-4}$ alkylidene or $C_{1-4}$ alkyl.

When $R^1$ represents an aroyl, or aroyl$C_{1-4}$alkyl, the aryl moiety may be selected from an optionally substituted phenyl ring or an optionally substituted 5- or 6-membered heterocyclic ring. In the group $R^1$ an aryl moiety may be optionally substituted by one or more substituents selected from hydrogen, halogen, amino, cyano, $C_{1-4}$alkyl, $C_{1-4}$alkylamino, $C_{1-4}$dialkylamino, $C_{1-4}$alkylamido, $C_{1-4}$ alkanoyl, or $R^5R^6NCO$ where each of $R^5$ and $R^6$ independently represents a hydrogen atom or $C_{1-4}$alkyl group.

A halogen atom present in the compounds of formula (I) may be fluorine, chlorine, bromine or iodine.

An optionally substituted 5- or 6-membered heterocyclic aromatic ring, as defined for any of the groups Ar, $Ar^1$ or $Ar^2$ may contain from 1 to 4 heteroatoms selected from O, N or S. When the ring contains 2-4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, pyrazolyl, isothiazolyl, and isoxazolyl.

Examples of bicyclic, for example bicyclic aromatic or heteroaromatic, ring systems for Ar include naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl, isoquinolinyl, pyrazolo[1,5-a]pyrimidyl, pyrrolo[3,2-b]pyridyl, pyrrolo[3,2-c]pyridyl, thieno[3,2-b]thiophenyl, 1,2-dihydro-2-oxo-quinolinyl, 3,4-dihydro-3-oxo-2H-benzoxazinyl, 1,2-dihydro-2-oxo-3H-indolyl.

Alternatively, Ar and $Ar^2$ may be optionally substituted by one or more 5- or 6-membered heterocyclic rings, as defined above, optionally substituted by a $C_{1-2}$ alkyl or $R^7R^8N$- group; wherein $R^7$ and $R^8$ are as defined above.

In the rings Ar and $Ar^2$ substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids e.g., hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other non-physiologically acceptable salts e.g., oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Most preferred compounds of the present invention include:

N-{4-[2-(-[(1R,8S)-11-azatricyclo[6.2.1.02,7]undeca-2,4,6-trien-11-yl)-ethyl]-cyclohexyl}-2-[2-({4-[2-(-[(1R,8S)-11-azatricyclo[6.2.1.02,7]undeca-2,4,6-trien-11-yl)-ethyl]-cyclohexylcarbamoyl}-methyl)-phenyl]-acetamide;

2,2'-benzene-1,3-diylbis[N-(trans-4-{2-[(1R,8S)-11-azatricyclo[6.2.1.0$^{2,7}$]undeca-2,4,6-trien-11-yl] ethyl}cyclohexyl)acetamide];

N-(trans-4-{2-[(1R,8S)-11-azatricyclo[6.2.1.0$^{2,7}$]undeca-2,4,6-trien-11-yl]ethyl}cyclohexyl)-N'-{4-[({[(trans-4-{2-[(1R,8S)-11-azatricyclo[6.2.1.0$^{2,7}$]undeca-2,4,6-trien-11-yl]ethyl}cyclohexyl)amino]carbonyl}amino)methyl]phenyl}urea;

N,N''-(benzene-1,3-diyldimethanediyl)bis[N-(trans-4-{2-[(1R,8S)-11-azatricyclo[6.2.1.0$^{2,7}$]undeca-2,4,6-trien-11-yl]ethyl}cyclohexyl)urea];

N',N'''-1,2-propanediylbis[N-(trans-4-{2-[(1R,8S)-11-azatricyclo[6.2.1.0$^{2,7}$]undeca-2,4,6-trien-11-yl] ethyl}cyclohexyl)urea];

N',N'''-1,6-hexanediylbis[N-(trans-4-{2-[(1R,8S)-11-azatricyclo[6.2.1.0$^{2,7}$]undeca-2,4,6-trien-11-yl] ethyl}cyclohexyl)urea];

N',N'''-[(methylimino)di-2,1-ethanediyl]bis[N-(trans-4-{2-[(1R,8S)-11-azatricyclo[6.2.1.0$^{2,7}$]undeca-2,4,6-trien-11-yl]ethyl}cyclohexyl)urea];

N',N'''-1,2-butanediylbis[N-(trans-4-{2-[(1R,8S)-11-azatricyclo[6.2.1.0$^{2,7}$]undeca-2,4,6-trien-11-yl] ethyl}cyclohexyl)urea];

N-(trans-4-{2-[(1R,8S)-11-azatricyclo[6.2.1.0$^{2,7}$]undeca-2,4,6-trien-11-yl ]ethyl}cyclohexyl)-N''-{15-[(trans-4-{2-[(1R,8S)-11-azatricyclo[6.2.1.0$^{2,7}$]undeca-2,4,6-trien-11-yl]ethyl}cyclohexyl)amino]-15-oxo-4,7,10-trioxa-14-azapentadec-1-yl}urea;

N',N'''1,4-butanediylbis[N-(trans-4-{2-[(1R,8S)-11-azatricyclo[6.2.1.0$^{2,7}$]undeca-2,4,6-trien-11-yl] ethyl}cyclohexyl)urea];

N',N'''-(thiodi-2,1-ethanediyl)bis[N-(trans-4-{2-[(1R,8S)-11-azatricyclo[6.2.1.0$^{2,7}$]undeca-2,4,6-trien-11-yl] ethyl}cyclohexyl)urea];

N',N'''-1,2-ethanediylbis[N-(trans-4-{2-[(1R,8S)-11-azatricyclo[6.2.1.0$^{2,7}$]undeca-2,4,6-trien-11-yl] ethyl}cyclohexyl)urea];

N-(trans-4-{2-[(1R,8S)-11-azatricyclo[6.2.1.0$^{2,7}$]undeca-2,4,6-trien-11-yl]ethyl}cyclohexyl)-N'-[3-({[(trans-4-{2-[(1R,8S)-11-azatricyclo[6.2.1.0$^{2,7}$]undeca-2,4,6-trien-11-yl]ethyl}cyclohexyl)amino]carbonyl}amino)-2,2-dimethylpropyl]urea;

N',N'''-1,2-cyclohexanediylbis[N-(trans-4-{2-[(1R,8S)-11-azatricyclo[6.2.1.0$^{2,7}$]undeca-2,4,6-trien-11-yl] ethyl}cyclohexyl)urea];

2,2'-benzene-1,4-diylbis[N-(trans-4-{2-[(1R,8S)-11-azatricyclo[6.2.1.0$^{2,7}$]undeca-2,4,6-trien-11-yl] ethyl}cyclohexyl)acetamide] trifluoroacetate;

2,2'-benzene-1,3-diylbis[N-(trans-4-{2-[(1R,8S)-11-azatricyclo[6.2.1.0$^{2,7}$]undeca-2,4,6-trien-11-yl] ethyl}cyclohexyl)acetamide] trifluoroacetate;

N-(trans-4-{2-[(1R,8S)-11-azatricyclo[6.2.1.0$^{2,7}$]undeca-2,4,6-trien-11-yl]ethyl}cyclohexyl)-N'-{([5-({[2-({[(trans-4-{2-[(1R,8S)-11-azatricyclo[6.2.1.0$^{2,7}$]undeca-2,4,6-trien-11-yl]ethyl{cyclohexyl)amino]carbony{amino)ethyl]thio}methyl)-2-furanyl]methyl}urea;

N',N'''-(2,3-naphthalenediyldimethanediyl)bis[N-(trans-4-(2-[(1R,8S)-11-azatricyclo[6.2.1.0$^{2,7}$]undeca-2,4,6-trien-11-yl]ethyl}cyclohexyl)urea];

N',N'''-1,12-dodecanediylbis[N-(trans-4-{2-[(1R,8S)-11-azatricyclo[6.2.1.0$^{2,7}$]undeca-2,4,6-trien-11-yl] ethyl}cyclohexyl)urea trifluoroacetate;

N',N'''-[benzene-1,2-diylbis(oxy-2,1-ethanediyl)]bis[N-(trans-4-{2-((1R,8S)-11-azatricyclo[6.2.1.0$^{2,7}$]undeca-2,4,6-trien-11-yl]ethyl}cyclohexyl)urea] trifluoroacetate;

N',N'''-(benzene-1,3-diyldi-2,1-ethanediyl)bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-(benzene-1,4-diyldi-2,1-ethanediyl)bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-(1,3-cyclohexanediyldimethanediyl)bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-1,11-undecanediylbis[N-(trans-4-{2-[(1R,8S)-11-azatricyclo[6.2.1.0$^{2,7}$]undeca-2,4,6-trien-11-yl] ethyl}cyclohexyl)urea] trifluoroacetate;

N',N'''-1,10-decanediylbis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-1,8-octanediylbis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-[1,1'-bi(cyclohexyl)-4,4'-diylbis(oxy-2,1-ethanediyl)]bis[N-(trans-4-{2-[(1R,8S)-11-azatricyclo[6.2.1.0$^{2,7}$]undeca-2,4,6-trien-11-yl]ethyl}cyclohexyl)urea];

N',N'''-(dithiodi-3,1-propanediyl)bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate and pharmaceutically acceptable salts thereof.

Preferred compounds of the present invention include:

N',N'''-(1,4-cyclohexanediyldimethanediyl)bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-[3-(1H-indol-3-yl)-1,2-propanediyl]bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-1,7-heptanediylbis[N-(trans-4-{2-[(1R,8S)-11-azatricyclo[6.2.1.0$^{2,7}$]undeca2,4,6-trien-11-yl]ethyl}cyclohexyl)urea] trifluoroacetate;

N-(trans-4-{2-[(1R,8S)-11-azatricyclo[6.2.1.0$^{2,7}$]undeca-2,4,6-trien-11-yl]ethyl}cyclohexyl)-N'-[2-({[(trans-4-{2-[(1R,8S)-11-azatricyclo[6.2.1.0 2,7]undeca-2,4,6-trien-1-yl]ethyl}cyclohexyl)amino]carbonyl}amino)-3-cyclohexyl-2-(hydroxymethyl)propy urea trifluoroacetate;

N',N'-[oxybis(benzene-4,1-diyl-1,1-ethanediyl)]bis[N-(trans-4-{2-[(1R,8S)-11-]azatricyclo[6.2.1.0$^{2,7}$]undeca-2,4,6-trien-11-yl]ethyl}cyclohexyl)urea] trifluoroacetate;

N',N''-oxybis(benzene-4,1-diyl-1,1-propanediyl)]bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-[(E)-1,2-ethenediylbis(benzene-4,1-diyl-methanediyl)]bis[N-(trans-4-{2-[(1R,8S 11-azatricyclo[6.2.1.0$^{2,7}$]undeca-2,4,6-trien-11-yl]ethyl}cyclohexyl)urea]trifluoroacetate;

N',N'''-[(1R,2R)-1,2-diphenyl-1,2-ethanediyl]bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-(9,10-anthracenediyldi-2,1-ethanediyl)bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate;

N',N'''-2,11-dodecanediylbis[N-(trans-4-{2-[(1R,8S)-11-azatricyclo[6.2.1.0$^{2,7}$]undeca2,4,6-trien-11-yl]ethyl}cyclohexyl)urea] trifluoroacetate;

N',N'''-(dithiodi-2,1-ethanediyl)bis[N-(trans-4-{2-[(1R,8S)-11-azatricyclo[6.2.1.0$^{2,7}$]undeca-2,4,6-trien-11-yl]ethyl}cyclohexyl)urea];

N~3~-{[(trans-4-{2-[(1R,8S)-11-azatricyclo[6.2.1.0$^{2,7}$]undeca-2,4,6-trien-11-yl]ethyl}cyclohexyl)amino]carbonyl}-N~1~-[3-({[(trans-4-{2-[(1R,8S)-11-azatricyclo[6.2.1.0$^{2,7}$]undeca-2,4,6-trien-11-yl]ethyl}cyclohexyl)amino]carbonyl}amino)propyl]-beta-alaninamide;

N',N'''-2-butyne-1,4-diylbis[N-(trans-4-{2-[(1R,8S)-11-azatricyclo[6.2.1.0$^{2,7}$]undeca2,4,6-trien-11-yl]ethyl}cyclohexyl)urea];

N',N'''-1,2-cyclopropanediylbis[N-(trans-4-{2-[(1R,8S)-11-azatricyclo[6.2.1.0$^{2,7}$]undeca-2,4,6-trien-11-yl]ethyl}cyclohexyl)urea];

N',N'''-2,3-butanediylbis[N-(trans-4-{2-[(1R,8S)-11-azatricyclo[6.2.1.0$^{2,7}$]undeca-2,4,6-trien-11-yl]ethyl}cyclohexyl)urea];

N',N'''-[1,2-ethanediylbis(oxy-2,1-ethanediyl)]bis[N-(trans-4-{2-[(1R,8S)-11-azatricyclo[6.2.1.0$^{2,7}$]undeca-2,4,6-trien-11-yl]ethyl}cyclohexyl)urea];

N',N'''-1,3-propanediylbis[N-(trans-4-{2-[(1R,8S)-11-azatricyclo[6.2.1.0$^{2,7}$]undeca-2,4,6-trien-11-yl]ethyl}cyclohexyl)urea];

N',N'''-1,9-nonanediylbis[N-(trans-4-{2-[(1R,8S)-11-azatricyclo[6.2.1.0$^{2,7}$]undeca-2,4,6-trien-11-yl]ethyl}cyclohexyl)urea];

N-(trans-4-{2-[(1R,8S)-11-azatricyclo[6.2.1.0$^{2,7}$]undeca-2,4,6-trien-11-yl]ethyl}cyclohexyl)-N'-(3-{10-[2-({[(trans-4-{2-[(1R,8S)-11-azatricyclo[6.2.1.0$^{2,7}$]undeca-2,4,6-trien-11-yl]ethyl}cyclohexyl)amino]carbonyl}amino)ethyl]-9-anthracenyl}propyl)urea;

N-(trans-4-{2-[(1R,8S)-11-azatricyclo[6.2.1.0$^{2,7}$]undeca-2,4,6-trien-11-yl]ethyl}cyclohexyl)-N'-{3-[[4-({[(trans-4-{2-[(1R,8S)-11-azatricyclo[6.2.1.0$^{2,7}$]undeca-2,4,6-trien-11-yl]ethy{cyclohexyl)amino]carbony}amino)butyl](phenylmethyl)amino]propyl}urea;

N',N'''-1,5-pentanediylbis[N-(trans-4-{2-[(1R,8S)-11-azatricyclo[6.2.1.0$^{2,7}$]undeca-2,4,6-trien-11-yl]ethyl}cyclohexyl)urea];

N',N'''-(3-oxo-1,5-pentanediyl)bis[N-(trans-4-{2-[(1R,8S)-11-azatricyclo[6.2.1.0$^{2,7}$]undeca-2,4,6-trien-11-yl]ethyl}cyclohexyl)urea];

N',N'''-(dithiodi-4,1-butanediyl)bis[N-(trans-4-{2-[(1R,8S)-11-azatricyclo[6.2.1.0$^{2,7}$]undeca-2,4,6-trien-11-yl]ethyl}cyclohexyl)urea];

methyl N~2~,N-6~bis{[(trans-4-{2-[(1R,8S)-11-azatricyclo[6.2.1.0$^{2,7}$]undeca-2,4,6-trien-11-yl]ethyl}cyclohexyl)amino]carbonyl}-L-lysinate;

ethyl N~2~,N~6~-bis{[(trans-4-{2-[(1R,8S)-11-azatricyclo[6.2.1.0$^{2,7}$]-trien-11-yl]ethyl}cyclohexyl)amino]carbonyl}lysinate;

N',N''-[benzene-1,3-diylbis(oxy-3,1-propanediyl)]bis[N-(trans-4-(2-[(1R,8S)-11-azatricyclo[6.2.1.0$^{2,7}$]undeca-2,4,6-trien-11-yl]ethyl}cyclohexyl)urea];

N',N'''-[benzene-1,2-diylbis(oxy-3,1-propanediyl)]bis[N-(trans-4-{2-[(1R,8S)-11-azatricyclo[6.2.1.0$^{2,7}$]undeca-2,4,6-trien-11-yl]ethyl}cyclohexyl)urea];

N',N'''-[(1R,7R)-tricyclo[5.2.1.0~2,6~]decane-3,8-diyldimethanediyl]bis[N-(trans-4-{2[(1R,8S)-11-azatricyclo[6.2.1.0$^{2,7}$]undeca-2,4,6-trien-11-yl]ethyl}cyclohexyl)urea];

N',N'''-[(methylimino)di-3,1-propanediyl]bis[N-(trans-4-{2-[(1R,8S)-11-azatricyclo[6.2.1.0$^{2,7}$]undeca-2,4,6-trien-11-yl]ethyl}cyclohexyl)urea] trifluoroacetate (2E)-N-(trans-4-{2-[(1R,8S)-11-azatricyclo[6.2.1.0$^{2,7}$]undeca-2,4,6-trien-11-yl]ethyl}cyclohexyl)-4-oxo-4-phenyl-2-butenamide;

N,N'-bis(trans-4-{2-[(1R,8S)-11-azatricyclo[6.2.1.0$^{2,7}$]undeca-2,4,6-trien-11-yl]ethyl}cyclohexyl)-2,6-pyridinedicarboxamide trifluoroacetate;

2,2'-oxybis[N-(trans-4-{2-[(1R,8S)-11-azatricyclo[6.2.1.0$^{2,7}$]undeca-2,4,6-trien-11-yl]ethyl}cyclohexyl)acetamide] trifluoroacetate;

N,N'-bis(trans-4-{2-[(1R,8S)-11-azatricyclo[6.2.1.0$^{2,7}$]undeca-2,4,6-trien-11-yl]ethyl}cyclohexyl)-2,3-pyrazinedicarboxamide trifluoroacetate;

N,N'-bis(trans-4-{2-[(1R,8S)-11-azatricyclo[6.2.1.0$^{2,7}$]undeca-2,4,6-trien-11-yl]ethyl}cyclohexyl)-3,4-pyridinedicarboxamide trifluoroacetate;

N,N'-bis(trans-4-{2-[(1R,8S)-11-azatricyclo[6.2.1.0$^{2,7}$]undeca-2,4,6-trien-11-yl]ethyl}cyclohexyl)-1,3-benzenedicarboxamide trifluoroacetate;

N,N'-bis(trans-4-{2-[(1R,8S)-11-azatricyclo[6.2.1.0$^{2,7}$]undeca-2,4,6-trien-11-yl]ethyl}cyclohexyl)-3,5-pyridinedicarboxamide trifluoroacetate;

2,2'-(1,1-cyclopentanediyl)bis[N-(trans-4-{2-[(1R,8S)-11-azatricyclo[6.2.1.0$^{2,7}$]undeca-2,4,6-trien-11-yl]ethyl}cyclohexyl)acetamide]trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,3-dimethylbutanediamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,5-thiophenedicarboxamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2-phenylbutanediamide trifluoroacetate;

N-(trans-4-{2-[(1R,8S)-11-azatricyclo[6.2.1.0$^{2,7}$]undeca-2,4,6-trien-11-yl]ethyl}cyclohexyl)-4-({2-[(trans-4-{2-[(1R,8S)-11-azatricyclo[6.2.1.0$^{2,7}$]undeca-2,4,6-trien-11-yl]ethyl}cyclohexyl)amino]-2-oxoethyl}oxy)benzamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-3,3-dimethylpentanediamide trifluoroacetate;

2,2'-(methylimino)bis[N-(trans-4-{2-[(1R,8S)-11-azatricyclo[6.2.1.0$^{2,7}$]undeca-2,4,6-trien-11-yl]ethyl}cyclohexyl)acetamide] trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,3-thiophenedicarboxamide trifluoroacetate;

N-(trans-4-{2-[(1R,8S)-11-azatricyclo[6.2.1.0$^{2,7}$]undeca-2,4,6-trien-11-yl]ethyl}cyclohexyl)-2-{3-[(trans-4-{2-[(1R,8S)-11-azatricyclo[6.2.1.0$^{2,7}$]undeca-2,4,6-trien-11-yl]ethyl}cyclohexyl)amino]-3-oxopropyl}benzamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,5-furandicarboxamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-1,2-cyclohexanedicarboxamide trifluoroacetate;

N,N'-bis(trans-4-(2-[(1R,8S)-11-azatricyclo[6.2.1.0$^{2,7}$]un-deca-2,4,6-trien-11-yl]ethyl}cyclohexyl)-1,3-cyclohexanedicarboxamide trifluoroacetate;

N-(trans-4-{2-[(1R,8S)-11-azatricyclo[6.2.1.0$^{2,7}$]undeca-2,4,6-trien-11-yl]ethyl}cyclohexyl)-4-{3-[(trans-4-{2-[(1R,8S)-11-azatricyclo[6.2.1.0$^{2,7}$]undcea-2,4,6-trien-11-yl]ethyl}cyclohexyl)amino]-3-oxopropyl}benzamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,2-dimethyl-1,3-cyclobutanedicarboxamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-1,3-cyclopentanedicarboxamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,2-dimethylbutanediamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2-(phenylmethyl)propanediamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,2-diethylpropanediamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-1,2-cyclopropanedicarboxamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-1,4-cyclohexanedicarboxamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)butanediamide trifluoroacetate;

N,N'-bis(trans-4-{2-[(1R,8S)-11-azatricyclo[6.2.1.0$^{2,7}$]un-deca-2,4,6-trien-11-yl]ethyl}cyclohexyl)-2,3-pyridinedicarboxamide trifluoroacetate and pharmaceutically acceptable salts thereof.

The following terms, as used herein, refer to:

"optionally substituted"—one or more substituents selected from: halo; hydroxy; hydroxy substituted $C_{1-10}$alkyl; $C_{1-10}$ alkoxy, such as methoxy or ethoxy; $S(O)_{m'}C_{1-10}$alkyl, wherein m' is 0, 1 or 2, such as methyl thio, methyl sulfinyl or methyl sulfonyl; amino, mono & di-substituted amino, such as in the $NR^4R^5$ group wherein $R^4$ and $R^5$ independently are hydrogen or $C_{1-4}$alkyl; $NHC(O)R^4$; $C(O)NR^4R^5$; $C(O)OH$; $C(O)OR^4$; $S(O)_2NR^4R^5$; $NHS(O)_2R^{20}$, $C_{1-10}$ alkyl, such as methyl, ethyl, propyl, isopropyl, or t-butyl; halosubstituted $C_{1-10}$ alkyl, such $CF_3$;

"halo"—all halogens, that is chloro, fluoro, bromo and iodo.

"$C_{1-10}$alkyl" or "alkyl" is used to mean both straight and branched chain moieties, optionally substituted, of 1 to 10 carbon atoms, unless the chain length is otherwise limited, including, but not limited to, methyl, ethyl, n-propyl, isopropyl, n-butyl, sec-butyl, isobutyl, tert-butyl, n-pentyl and the like;

"cycloalkyl" is used herein to mean an optionally substituted cyclic moiety, preferably of 3 to 8 carbons, including but not limited to cyclopropyl, cyclopentyl, cyclohexyl, and the like.

"heteroaryl" (on its own or in any combination, such as "heteroaryloxy", or "heteroaryl alkyl") — a 5-10 membered aromatic ring system, optionally substituted, in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

Particular compounds according to the invention include those specifically exemplified and named hereinafter.

METHODS OF PREPARATION

The compounds of Formula (I) may be obtained by applying synthetic procedures, some of which are illustrated in the Schemes below. The synthesis provided for these Schemes is applicable for producing compounds of Formula (I) having a variety of different $R^1$, $R^2$, $G^1$, $G^2$, X, Y and L groups which are reacted, employing substituents which are suitable protected, to achieve compatibility with the reactions outlined herein. Subsequent deprotection, in those cases, then affords compounds of the nature generally disclosed. Once the bicyclic amine core has been established, further compounds of these Formulas may be prepared by applying techniques for functional groups interconversion, well known in the art. While the Schemes are shown with compounds only of Formula (I), this is merely for illustration purpose only Scheme 1

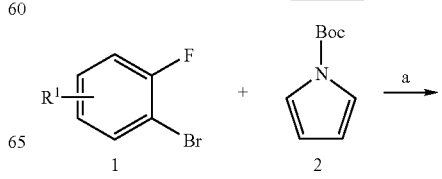

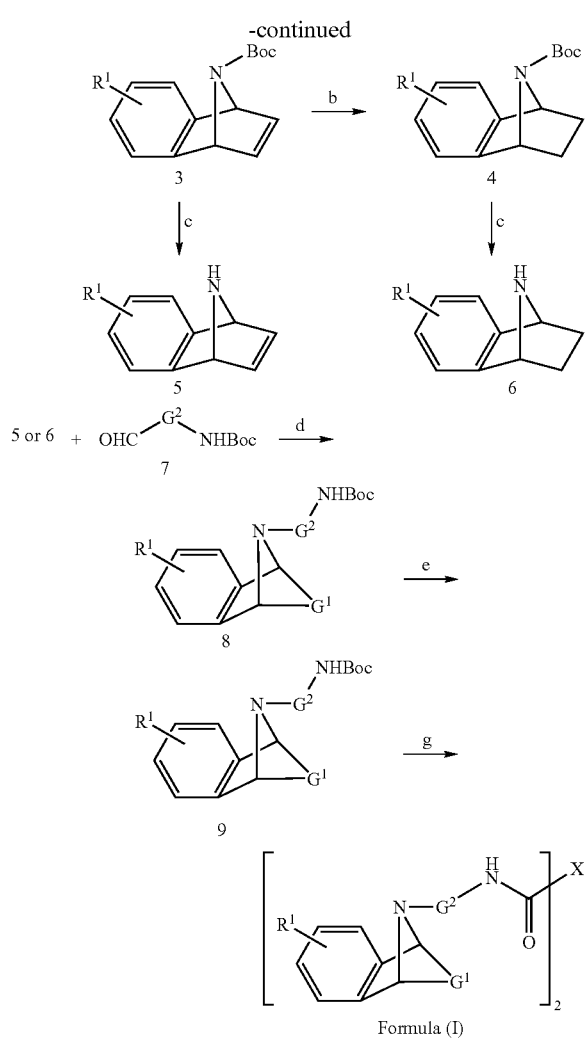

Reagents and conditions:
a) Mg, THF;
b) H₂, Pd/C, EtOH;
c) TFA, CH₂Cl₂;
d) NaBH(OAc)₃, (CH₂Cl)₂;
e) TFA, CH₂Cl₂;
f) Dicarboxylic acid 10, EDC•HCl, HOBt, diisopropylethylamine, CH₂Cl₂;
g) Diamine 11, triphosgene, CH₂Cl₂ or Diamine 11, p-NO₂-PhOCOCl, CH₂Cl₂ or diisocyante 12, DMF or Diacid 10, DPPA, DMF.

The desired compounds of formula (I) can be prepared as outlined in Scheme 1. Compounds 3 can be obtained via a benzyne reaction from suitable starting materials such as 2-fluorobromobenzenes and suitably N-protected pyrrole using carbamate protecting groups well known in the art such as the Boc group. The reaction can be effected using reagents such as magnesium or alkyl lithiums in suitable solvent such as THF or ether. Compounds 5 can be obtained by deprotection of the Boc group using standard methods such as treatment with trifluroacetic acid (TFA), dry HCl or iodotrimethylsilane (TMSI) in suitable aprotic solvents. The compounds 4 can be prepared by subjecting 3 to standard reductive conditions well known to those skilled in the art such as treatment with hydrogen gas in the presence of a catalytic amount of palladium on carbon in a suitable solvent such as ethanol. Deprotection to yield compounds 6 can be effected in a manner similar to that described for compounds 5. Compounds 8 can be obtained by reacting 5 or 6 with aldehydes 7 under the well known reductive amination conditions using suitable reagents such as sodium triacetoxyborohydride. The compounds 9 can then be prepared by deprotection of 8 using the conditions listed for the preparation of the compounds 5. Compounds of formula (I) which are of the amide type, can be made by treating compounds 9 with dicarboxylic acids 10 under suitable amide coupling conditions well known to those skilled in the art such as 1-hydroxybenzotriazole hydrate (HOBt), 1-(3-dimethylaminopropyl)-3-ethylcarbodiimide hydrochloride (EDC-HCl) and diisopropylethylamine(DIEA) in dichloromethane. Compounds of formula (I) which are of the urea type, can be made by treating compounds 9 with a suitable coupling reagent such as triphosgene or 4-nitrophenylchloroformate followed by diamines 11 or by treating compounds 9 with diisocyanates 12, which may have been formed in situ via a Curtius rearrangement effected by exposing carboxylic acids 10 a reagent such as diphenylphosphoryl azide, in a suitable solvent such as DMF.

Scheme 2

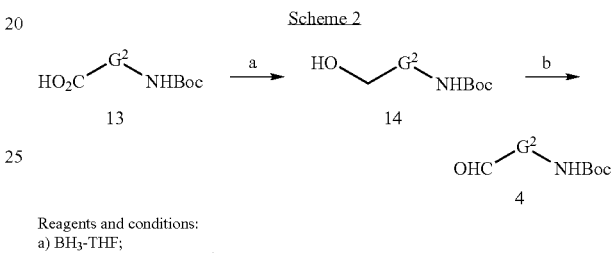

Reagents and conditions:
a) BH₃-THF;
b) PCC or TPAP, NMO, 4ÅMs

Aldehydes 4 may be prepared from carboxylic acids 13 by reduction to the alcohol 14 using standard conditions such as borane-THF complex (BH₃-THF) followed by oxidation to the aldehyde using standard conditions well know to those skilled in the art such as pyridinium chlorochromate (PCC), tetrapropylammonium perruthenate (TPAP), Swern oxidation or Dess-Martin periodinane. Alternatively, compounds 4 may be prepared according to Stemp et al. (*J. Med. Chem.* 2000, 43, 1878-85).

Scheme 3

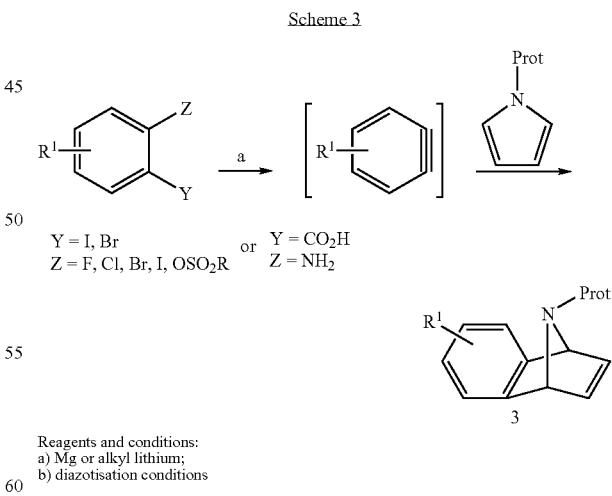

Reagents and conditions:
a) Mg or alkyl lithium;
b) diazotisation conditions

If suitable 2-fluorobromobenzenes are not commercially available, the benzyne reaction to form compounds 3 can be performed with other 1,2-substituted benzenes: 1) For those in which the substituent Y is either iodine or bromine and the substituent Z is any halogen or an aryl sulfonate the benzyne forming reaction may be effected by treatment with either magnesium or an alkyl lithium; 2) For 2-aminobenzoic acids, the benzyne may be formed by subjecting the substrate to diazotisation reagents well know in the art such as isoamylnitrite or sodium nitrite in acidic media.

SYNTHETIC EXAMPLES

Example 1

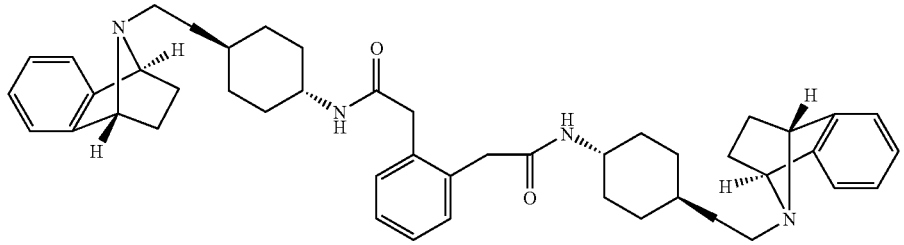

2,2'-benzene-1,2-diylbis[N-(trans-4-{2-[(1R,8S)-11-azatricyclo[6.2.1.0$^{2,7}$]undeca-2,4,6-trien-11-yl]ethyl}cyclohexyl)acetamide]

1a) {4-[2-(-[(1R,8S)-11-azatricyclo[6.2.1.0$^{2,7}$]undeca-2,4,6-trien-11-yl)-ethyl]-cyclohexyl}-carbamic acid tert-butyl ester To a solution of (1R,8S)-11-azatricyclo[6.2.1.0$^{2,7}$]undeca-2,4,6-triene, which was made according to *J. of Organic Chemistry*, 1966, 31, 764-767, (1.237 g, 8.52 mmol) in 75 mL of 1,2-dichloroethane, was added [4-(2-oxo-ethyl)-cyclohexyl]-carbamic acid tert-butyl ester (2.056 g, 8.52 mmol) and sodium triacetoxyborohydride (2.708 g, 12.78 mmol). The mixture was stirred at RT overnight, diluted with dichloromethane. The resulting mixture was washed with saturated aqueous K$_2$CO$_3$, extracted with dichloromethane, dried over magnesium sulfate and the solven twas removed in vacuo. The resulting crude material was purified via filtering through a silica pad using ethyl acetate as mobile phase to give 2.681 g (85%) of the title compound. LCMS m/z 371.2 (M+H).

1b) 4-[2-(-[(1R,8S)-11-azatricyclo[6.2.1.0$^{2,7}$]undeca-2,4,6-trien-11-yl)-ethyl]-cyclohexylamine To the solution of the crude {4-[2-(-[(1R,8S)-11-azatricyclo[6.2.1.0$^{2,7}$]undeca-2,4,6-trien-11-yl)-ethyl]-cyclohexyl}-carbamic acid tert-butyl ester (2.681 g, 7.23 mmol) in 60 mL of dichloromethane was added 4.5 mL of TFA. The mixture was stirred at RT overnight. The solvent was evaporated to give the crude TFA salt. This material was partitioned between saturated aqueous K$_2$CO$_3$ and CH$_2$Cl$_2$. The mixture was extracted with CH$_2$Cl$_2$ (2X). The combined organic phase was washed with brine, dried over magnesium sulfate and the solvent was removed in vacuo to give the title compound 1.759 g (90%). LCMS m/z 271.2 (M+H).

1c) N-{4-[2-(-[(1R,8S)-11-azatricyclo[6.2.1.0$^{2,7}$]undeca-2,4,6-trien-11-yl)-ethyl]-cyclohexyl}-2-[2-({4-[2-(-[(1R,8S)-11-azatricyclo[6.2.1.0$^{2,7}$]undeca-2,4,6-trien-11yl)-ethyl]-cyclohexylcarbamoyl}-methyl)-phenyl]-acetamide The mixture of (2-carboxymethyl-phenyl)-acetic acid (154mg, 0.79 mmol), 4-[2-(-[(1R,8S)-11-azatricyclo[6.2.1.0$^{2,7}$]undeca-2,4,6-trien-11-yl)-ethyl]-cyclohexylamin (425mg, 1.57 mmol), EDC (301 mg, 1.57 mmol), HOBT (27 mg, 0.2 mmol) and DIPEA (0.45 mL, 3.16 mmol) in 25 mL of CHCl$_3$ was stirred at RT overnight. The mixture was diluted with CH$_2$Cl$_2$, washed with water, brine and dried over MgSO$_4$. The solvent was removed in vacuo to yield the crude material, which was purified by triturating with ethyl acetate to give the desired product 99 mg (18%). LC-MS: m/z 699.4 (M+H).

Example 2

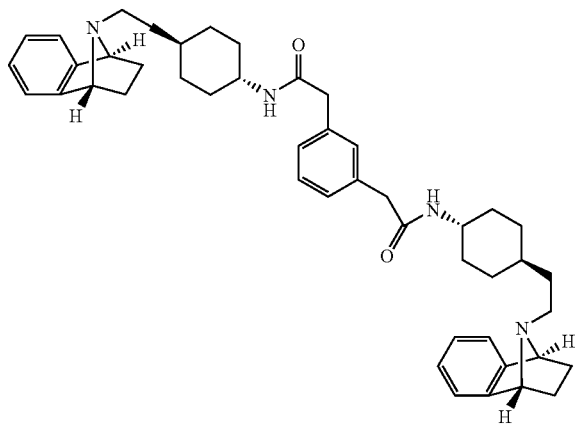

2,2'-benzene-1,3-diylbis[N-(trans-4-{2-[(1R,8S)-11-azatricyclo6.2.1.0$^{2,7}$]undeca-2,4,6-trien-11-yl]ethyl}cyclohexyl)acetamide]

Following the general procedure described in Example 1c, 4-[2-(-[(1R,8S)-11-azatricyclo[6.2.1.0$^{2,7}$]undeca-2,4,6-trien-11-yl)-ethyl]-cyclohexylamine (441 mg, 1.63 mmol) coupled with (2-carboxymethyl-phenyl)-acetic acid (158 mg, 0.81 mmol) to give the titled compound 255 mg (45%). LCMS m/z 699.4 (M+H).

Example 3

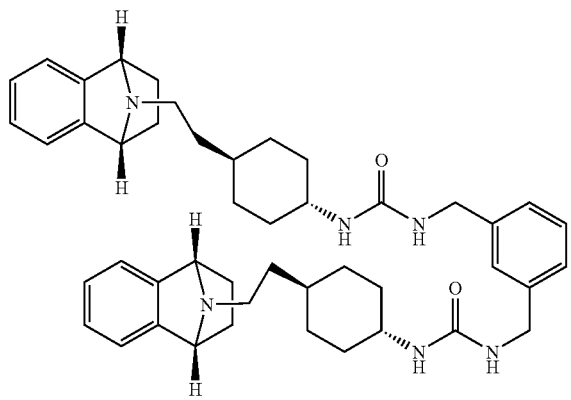

N,N''-(benzene-1,3-diyidimethanediyl)bis[N-(trans-4-{2-[(1R,8S)-11-azatricyclo[6.2.1.0$^{2,7}$]undeca-2,4,6-trien-11-yl]ethyl}cyclohexyl)urea]

The mixture of 4-[2-(-[(1R,8S)-11-azatricyclo[6.2.1.0$^{2,7}$]undeca-2,4,6-trien-11-yl)-ethyl]-cyclohexylamine (97 mg, 0.36 mmol) and 1-isocyanato-3-isocyanatomethyl-benzene (26 µL, 0.18 mmol) in 1.2 mL of DMF was stirred at RT overnight. Solid precipitated out of the solution by adding ethyl acetate. The mixture was filtered, the solid was washed with ethyl acetate and hexane to yield the title compound 46 mg (36%) as a white solid. LCMS m/z 715.4 (M+H).

Example 4

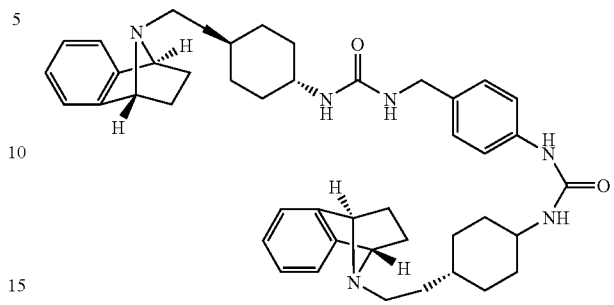

N-(trans-4-{2-[(1R,8S)-11-azatricyclo[6.2.1.0$^{2,7}$]undeca-2,4,6-trien-11yl]ethyl}cyclohexyl)-N-{-4-[({[(trans-4-{2-[(1R,8S)-11-azatricyclo[6.2.1.0$^{2,7}$]2,4,6-trien-11-yl]ethyl}cyclohexyl)amino]carbonyl}amino)methyl]phenyl}urea Following the general procedure described in Example 3, 4-[2-(-[(1R,8S)-11-azatricyclo[6.2.1.0$^{2,7}$]undeca-2,4,6-trien-11-yl)-ethyl]-cyclohexylamine (76 mg, 0.28 mmol) coupled with 1,3-bis(isocyanatomethyl)-benzene (22 µL, 0.14 mmol) to give the titled compound 45 mg (44%). LCMS m/z 729.6 (M+H).

In addition, following either the procedure for the preparation of Example 1 (diamides) or for the preparation of Example 3 (diureas), the following compounds (Examples 5-86) were synthesized and tested:

TABLE 1

| Example | X | LCMS (ES) m/z (M + H)⁺ (unless otherwise noted) | Comment |
|---|---|---|---|
| 5 |  | 667.0 |  |
| 6 |  | 709.0 |  |
| 7 |  | 710.0 |  |
| 8 |  | 681.0 |  |

TABLE 1-continued

| Example | X | LCMS (ES) m/z (M + H)+ (unless otherwise noted) | Comment |
| --- | --- | --- | --- |
| 9 | | 813.0 | |
| 10 | | 681.0 | |
| 11 | | 713.0 | |
| 12 | | 653.0 | |
| 13 | | 695.0 | |
| 14 | | 707.0 | |
| 15 | | 350.0 | double charged ion |
| 16 | | 350.0 | double charged ion |
| 17 | | 779.0 | |

TABLE 1-continued

| Example | X | LCMS (ES) m/z (M + H)+ (unless otherwise noted) | Comment |
|---------|---|---|---|
| 18 | | 779.0 | |
| 19 | | 793.0 | |
| 20 | | 779.0 | |
| 21 | | 765.0 | |
| 22 | | 737.0 | |
| 23 | | 877.0 | |
| 24 | | 773.0 | |
| 25 | | 789.0 | |
| 26 | | 757.0 | |

TABLE 1-continued

| Example | X | LCMS (ES) m/z (M + H)+ (unless otherwise noted) | Comment |
|---|---|---|---|
| 27 | | 757.0 | |
| 28 | | 735.0 | |
| 29 | | 735.0 | |
| 30 | | 782.0 | |
| 31 | | 723.0 | |
| 32 | | 779.0 | |
| 33 | | 849.0 | |

TABLE 1-continued
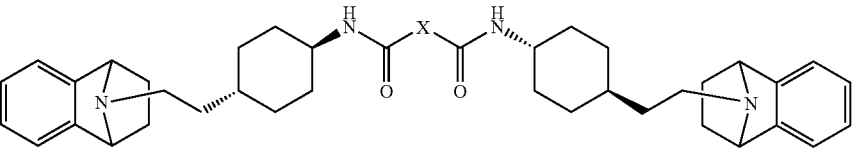
| Example | X | LCMS (ES) m/z (M + H)+ (unless otherwise noted) | Comment |
|---|---|---|---|
| 34 | 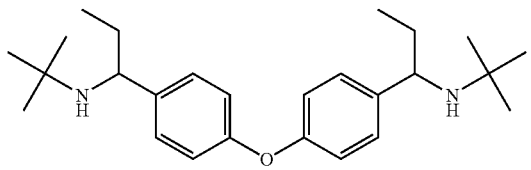 | 877.0 | |
| 35 | 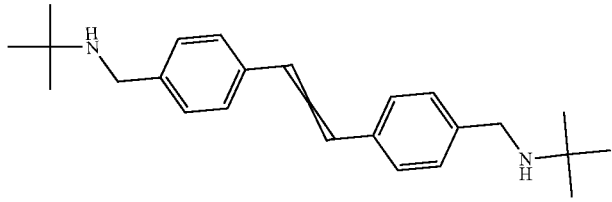 | 831.0 | |
| 36 | 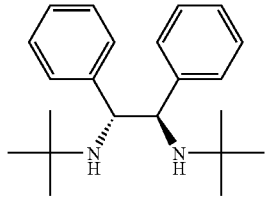 | 805.0 | |
| 37 | 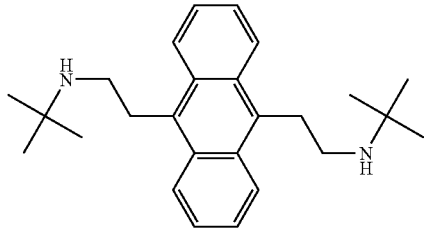 | 857.0 | |
| 38 | 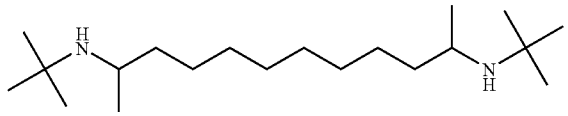 | 793.0 | |
| 39 | 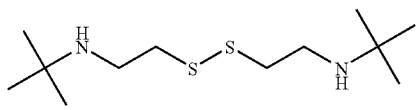 | 745.0 | |
| 40 | 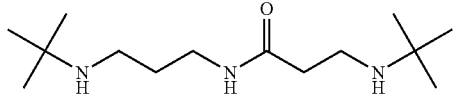 | 738.0 | |

TABLE 1-continued

| Example | X | LCMS (ES) m/z (M + H)+ (unless otherwise noted) | Comment |
|---|---|---|---|
| 41 | | 677.0 | |
| 42 | | 665.0 | |
| 43 | | 681.0 | |
| 44 | | 741.0 | |
| 45 | | 667.0 | |
| 46 | | 751.0 | |
| 47 | | 871.0 | |
| 48 | | 828.0 | |

TABLE 1-continued

| Example | X | LCMS (ES) m/z (M + H)+ (unless otherwise noted) | Comment |
|---|---|---|---|
| 49 | | 695.0 | |
| 50 | | 709.0 | |
| 51 | | 801.0 | |
| 52 | | 753.0 | |
| 53 | | 767.0 | |
| 54 | | 817.0 | |
| 55 | | 817.0 | |
| 56 | | 787.0 | |
| 57 | | 738.0 | |

TABLE 1-continued

| Example | X | LCMS (ES) m/z (M + H)+ (unless otherwise noted) | Comment |
|---|---|---|---|
| 58 | *tert-butyl-NH-cyclohexyl-NH-tert-butyl* | 707.0 | |
| 59 | *2,6-di-tert-butylpyridine* | 336.5 | double charged ion |
| 60 | *bis(neopentyl) ether* | 320.0 | double charged ion |
| 61 | *2,3-di-tert-butylpyrazine* | 337.0 | double charged ion |
| 62 | *3,4-di-tert-butylpyridine* | 336.5 | double charged ion |
| 63 | *1,3-di-tert-butylbenzene* | 336.0 | double charged ion |
| 64 | *3,5-di-tert-butylpyridine* | 336.5 | double charged ion |
| 65 | *1,1-di-neopentyl-cyclopentane* | 346.0 | double charged ion |

TABLE 1-continued
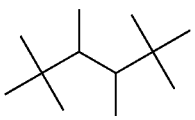
| Example | X | LCMS (ES) m/z (M + H)+ (unless otherwise noted) | Comment |
|---|---|---|---|
| 66 | 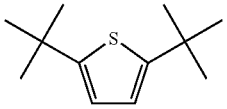 | 326.0 | double charged ion |
| 67 | 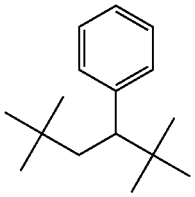 | 339.0 | double charged ion |
| 68 | 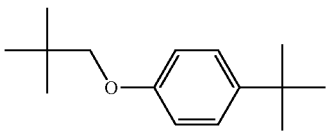 | 350.0 | double charged ion |
| 69 |  | 351.0 | double charged ion |
| 70 | 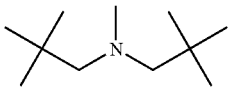 | 333.0 | double charged ion |
| 71 | 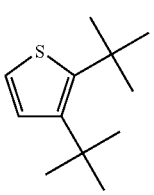 | 326.5 | double charged ion |
| 72 | 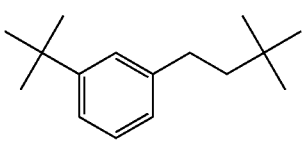 | 339.0 | double charged ion |
| 73 | 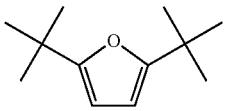 | 350.0 | double charged ion |
| 74 | | 331.0 | double charged ion |

TABLE 1-continued
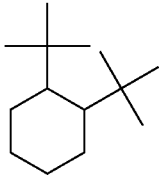
| Example | X | LCMS (ES) m/z (M + H)+ (unless otherwise noted) | Comment |
|---|---|---|---|
| 75 | 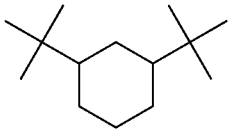 | 339.0 | double charged ion |
| 76 | 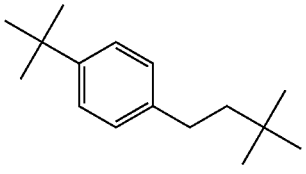 | 339.0 | double charged ion |
| 77 | 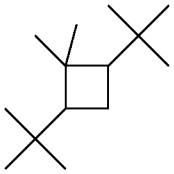 | 350.0 | double charged ion |
| 78 | 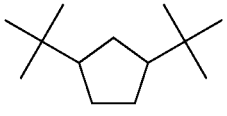 | 339.0 | double charged ion |
| 79 | 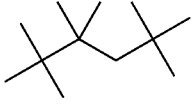 | 332.0 | double charged ion |
| 80 | 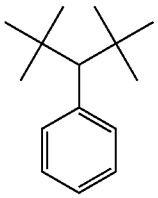 | 326.0 | double charged ion |
| 81 | 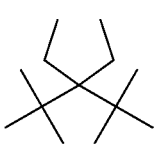 | 350.0 | double charged ion |
| 82 | | 333.0 | double charged ion |

TABLE 1-continued

| Example | X | LCMS (ES) m/z (M + H)⁺ (unless otherwise noted) | Comment |
|---|---|---|---|
| 83 | 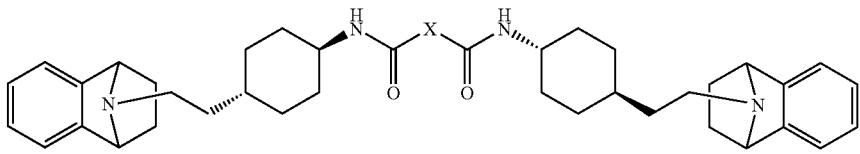 | 318.0 | double charged ion |
| 84 | 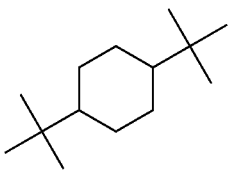 | 339.0 | double charged ion |
| 85 |  | 312.0 | double charged ion |
| 86 | 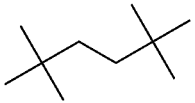 | 336.5 | double charged ion |

BIOLOGICAL EXAMPLES

The inhibitory effects of compounds at the $M_3$ mAChR of the present invention are determined by the following in vitro and in vivo functional assays:

Analysis of Inhibition of Receptor Activation by Calcium Mobilization:

Stimulation of mAChRs expressed on CHO cells were analyzed by montoring receptor-activated calcium mobilization as previously described (Sarau, H. M., R. S. Ames, J. Chambers, C. Ellis, N. Elshourbagy, J. J. Foley, D. B. Schmidit, R. M. Muccitelli, O. Jenkins, P. R. Murdock, N. C. Herrity, W. Halsey, G. Sathe, A. I. Muir, P. Nuthulaganti, G. M. Dytko, P. T. Buckley, S. Wilson, D. J. Bergasma, and D. W. Hay. 1999. Identification, molecular cloning, expression, and characterization of a cysteinyl leukotriene receptor. Mol Pharmacol 56:657-663). CHO cells stably expressing $M_3$ mAChRs were plated in 96 well black wall/clear bottom plates. After 18 to 24 hours, media was aspirated and replaced with 100 μl of load media (EMEM with Earl's salts, 0.1% RIA-grade BSA (Sigma, St. Louis Mo.), and 4 μM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 μl of assay buffer (0.1% gelatin (Sigma), 120 mM NaCl, 4.6 mM KCl, 1 mM $KH_2PO_4$, 25 mM $NaHCO_3$, 1.0 mM $CaCl_2$, 1.1 mM $MgCl_2$, 11 mM glucose, 20 mM HEPES (pH 7.4)). 50 μl of compound ($1\times10^{-11}$-$1\times10^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 μl of acetylcholine (0.1-10 nM final), prepared in buffer containing 0.1% BSA, at a rate of 50 μl/sec. Calcium mobilization, monitored as change in cytosolic calcium concentration, was measured as change in 566 nm emission intensity. The change in emission intensity is directly related to cytosolic calcium levels (Sullivan, E., E. M. Tucker, and I. L. Dale. 1999. Measurement of [Ca2+] using the Fluorometric Imaging Plate Reader (FLIPR). Methods Mol Biol 114:125-133). The emitted fluorescence from all 96 wells is measured simultaneously using a cooled CCD camera. Data points are collected every second. This data was then plotting and analyzed using GraphPad PRISM software.

Methacholine-induced Bronchoconstriction

Airway responsiveness to methacholine was determined in awake, unrestrained BalbC mice (n=6 each group). Barometric plethysmography was used to measure enhanced pause (Penh), a unitless measure that has been shown to correlate with the changes in airway resistance that occur during bronchial challenge with methacholine (Hamelmann, E., J. SCHWARZE, K. TAKEDA, A. OSHIBA, G. á. LARSEN, C. á. IRVIN, and E. á. GELFAND. 1997. Non-invasive Measurement of Airway Responsiveness in Allergic Mice Using Barometric Plethysmography. Am.J.Respir. Crit.Care Med. 156:766-775). Mice were pretreated with 50

μl of compound (0.003-10 μg/mouse) in 50 μl of vehicle (10% DMSO) intranasally, i.v., i.p. or p.o, and were then placed in the plethysmography chamber. Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software.

The present compounds are useful for treating a variety of indications, including but not limited to respiratory-tract disorders such as chronic obstructive lung disease, chronic bronchitis, asthma, chronic respiratory obstruction, pulmonary fibrosis, pulmonary emphysema, and allergic rhinitis; gastrointestinal-tract disorders such as irritable bowel syndrome, spasmodic colitis, gastroduodenal ulcers, gastrointestinal convulsions or hyperanakinesia, diverticulitis, pain accompanying spasms of gastrointestinal smooth musculature; urinary-tract disorders accompanying micturition disorders including neurogenic pollakisuria, neurogenic bladder, nocturnal enuresis, psychosomatic bladder, incontinence associated with bladder spasms or chronic cystitis, urinary urgency or pollakiuria, and motion sickness.

Methods of administering the present compounds will be readily apparent to the skilled artisan. Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 20 μg-10 mg of the compound of formula (I) optionally in combination with another therapeutically active ingredient. Alternatively, the compound of the invention may be presented without excipients.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant an inhaler having a reservoir form pack suitable for comprising multiple (un-metered doses) of medicament in dry powder form and including means for metering medicament dose from the reservoir to a delivery position. The metering means may for example comprise a metering cup, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disc-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Where the medicament container is an aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 μl, such as 25 μl, 50 μl or 63 μl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined therebetween and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085. Additionally, intra-nasal delivery of the present compounds is effective.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the medicament must be capable of resisting those forces in the nasal passages that function to remove particles from the nose. Such forces, referred to as 'mucociliary clearance', are recognised as being extremely effective in removing particles from the nose in a rapid manner, for example, within 10-30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors.

A suitable dosing regime for the formulation of the present invention when administered to the nose would be for the patient to inhale deeply subsequent to the nasal cavity being cleared. During inhalation the formulation would be applied to one nostril while the other is manually compressed. This procedure would then be repeated for the other nostril.

A preferable means for applying the formulation of the present invention to the nasal passages is by use of a pre-compression pump. Most preferably, the pre-compression pump will be a VP7 model manufactured by Valois SA. Such a pump is beneficial as it will ensure that the formulation is not released until a sufficient force has been applied, otherwise smaller doses may be applied. Another advantage of the pre-compression pump is that atomisation of the spray is ensured as it will not release the formulation until the threshold pressure for effectively atomising the spray has been achieved. Typically, the VP7 model may be used with a bottle capable of holding 10-50 ml of a formulation. Each spray will typically deliver 50-100 μl of such a formulation, therefore, the VP7 model is capable of providing at least 100 metered doses.

EXAMPLES OF NASAL FORMULATIONS

Example 1

Nasal formulation Containing Active

A formulation for intranasal delivery was prepared with ingredients as follows:

| | |
|---|---|
| | to 100% |
| Active | 0.1% w/w |
| Polysorbate 80 | 0.025% w/w |
| Avicel RC591 | 1.5% w/w |
| Dextrose | 5.0% w/w |
| BKC | 0.015% w/w |
| EDTA | 0.015% w/w |
| water | to 100% | in a total amount suitable for 120 actuations and the formulation was filled into a bottle fitted with a metering valve adapted to dispense 50 or 100 μl per actuation. The device was fitted into a nasal actuator (Valois).

Example 2

Nasal formulation containing active

A formulation for intranasal delivery was prepared with ingredients as follows:

| | |
|---|---|
| Active | 0.005% w/w |
| Tyloxapol | 2% w/w |
| dextrose | 5% w/w |
| BKC | 0.015% w/w |
| EDTA | 0.015% w/w |
| water | to 100% | in a total amount suitable for 120 actuations and the formulation was filled into a bottle (plastic or glass) fitted with a metering valve adapted to dispense 50 or 100 μl per actuation The device was fitted into a nasal actuator (Valois, e.g. VP3, VP7 or VP7D)

Example 3

Nasal Formulation Containing Active

A formulation for intranasal delivery was prepared with ingredients as follows:

| | |
|---|---|
| active | 0.05% w/w |
| Triton X-100 | 5% w/w |
| Dextrose | 4% w/w |
| BKC | 0.015% w/w |
| EDTA | 0.015% w/w |
| water | to 100% | in a total amount suitable for 120 actuations and the formulation was filled into a bottle fitted with a metering valve adapted to dispense 50 or 100 μl per actuation.

Example 4

Nasal Formulation Containing Active

| active | 0.05% w/w |
|---|---|
| Tyloxapol | 5% w/w |
| dextrose | 5% w/w |
| BKC | 0.015% w/w |
| EDTA | 0.015% w/w |
| water | to 100% | in a total amount suitable for 120 actuations and the formulation was filled into a bottle fitted with a metering valve adapted to dispense 50 or 100 µl per actuation The device was fitted into a nasal actuator (Valois).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula

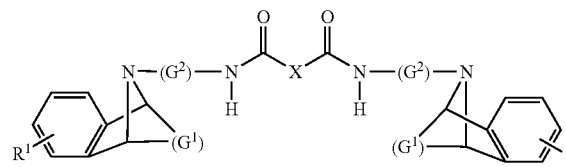

(I)

wherein:
R$^1$ is selected from the group consisting of hydrogen, halogen, C$_{1-4}$ alkyl, C14 alkanoyl and aroyl;
G$^1$ is CH$_2$—CH2 or CH=CH;
G$^2$ is C$_{4-7}$ alkyl or a group of the formula (a), (b) or (c):

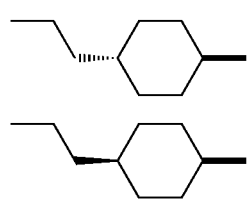

(a)

(b)

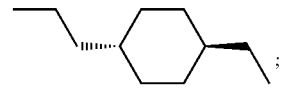

(c)

X is a group of the formula (d):

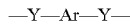

(d)

Y is, independently, selected from the group consisting of a bond, O, S, NR$^2$, —NR$^2$—C$_{1-4}$ alkyl-, and C$_{1-4}$ alkyl- each of these alkyl groups may contain a heteroatom selected from O, NR$^2$, or S;
R$^2$ is a hydrogen, C$_{1-4}$ alkyl or C$_{1-4}$ alkyl-aryl;
Ar is selected from the group consisting of an optionally substituted phenyl rings, optionally substituted 5- or 6-membered aromatic heterocyclic ring or an optionally substituted, fused bicyclic, tricyclic aromatic or heteroaromatic ring system.

2. A compound according to claim 1 selected from the group consisting of:
N-{4-[2-(-[(1R,8S)-11-azatricyclo[6.2.1.0$^{2,7}$]undeca-2,4,6-trien-11-yl)-ethyl]-cyclohexyl}-2-[2-({4-[2-(-[(1R,8S)-11-azatricyclo[6.2.1.0$^{2,7}$]undeca-2,4,6-trien-11-yl)-ethyl]-cyclohexylcarbamoyl}-methyl)-phenyl]-acetamide;
2,2'-benzene-1,3-diylbis[N-(trans-4-{2-[(1R,8S)-11-azatricyclo[6.2.1.0$^{2,7}$]undeca-2,4,6-trien-11-yl]ethyl}cyclohexyl)acetamide];
N-(trans-4-{2-[(1R,8S)-11-azatricyclo[6.2.1.0$^{2,7}$]undeca-2,4,6-trien-11-yl]ethyl}cyclohexyl)-N-{4-[({[(trans-4-{2-[(1R,8S)-11-azatricyclo[6.2.1.0$^{2,7}$]undeca-2,4,6-trien-11-yl]ethyl}cyclohexyl)amino]carbonyl}amino)methyl]phenyl}urea;
N,N''-(benzene-1,3-diyldimethanediyl)bis[N-(trans-4-{2-[(1R,8S)-11-azatricyclo[6.2.1.0$^{2,7}$]undeca-2,4,6-trien-11-yl]ethyl}cyclohexyl)urea]; and pharmaceutically acceptable salts thereof.

3. A pharmaceutical composition comprising a compound according to claim 1 and a pharmaceutically acceptable carrier thereof.

4. A method of treating a muscarinic acetylcholine receptor mediated disease selected from the group consisting of chronic obstructive lung disease, chronic bronchitis, asthma, chronic respiratory obstruction, pulmonary fibrosis, pulmonary emphysema and allergic rhinitis comprising administering an effective amount of a compound according to claim 1.

5. A method according to claim 4 wherein administration is via inhalation via the mouth or nose.

6. A method according to claim 5 wherein administration is via a medicament dispenser selected from a reservoir dry powder inhaler, a multi-dose dry powder inhaler or a metered dose inhaler.

7. A method according to claim 6 wherein the compound is administered to a human.

8. A method according to claim 7 wherein the compound has a duration of action of 12 hours or more.

9. A compound according to claim 1 wherein G$^2$ is of formula (a).

10. A compound according claim 1 wherein Ar is phenyl.

11. A compound according to claim 10 wherein Y is independently a C$_{1-4}$ alkyl.

12. A compound according to claim 11 wherein G$^1$ is CH=CH.

13. A compound according to claim 1 wherein $G^1$ is CH=CH.

14. A compound according to claim 1 wherein Ar is furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, pyrazolyl, isothiazolyl, or isoxazolyl.

15. A compound according to claim 13 wherein Ar is furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, pyrazolyl, isothiazolyl, or isoxazolyl.

16. A compound according to claim 1 wherein Ar is naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl, isoquinolinyl, pyrazolo[1,5-a]pyrimidyl, pyrrolo[3,2-b]pyridyl, pyrrolo[3,2-c]pyridyl, thieno[3,2-b]thiophenyl, 1,2-dihydro-2-oxo-quinolinyl, 3,4-dihydro-3-oxo-2H-benzoxazinyl, or 1,2-dihydro-2-oxo-3H-indolyl.

17. A compound according to claim 13 wherein Ar is naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl, isoquinolinyl, pyrazolo[1,5-a]pyrimidyl, pyrrolo[3,2-b]pyridyl, pyrrolo[3,2-c]pyridyl, thieno[3,2-b]thiophenyl, 1,2-dihydro-2-oxo-quinolinyl, 3,4-dihydro-3-oxo-2H-benzoxazinyl, or 1,2-dihydro-2-oxo-3H-indolyl.

18. A compound of the formula:

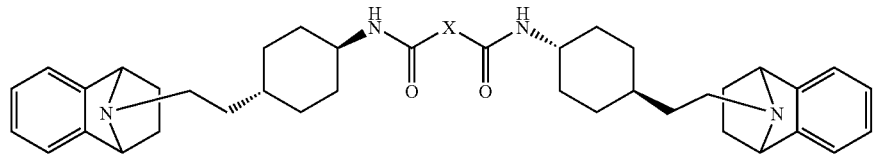

wherein X is selected from

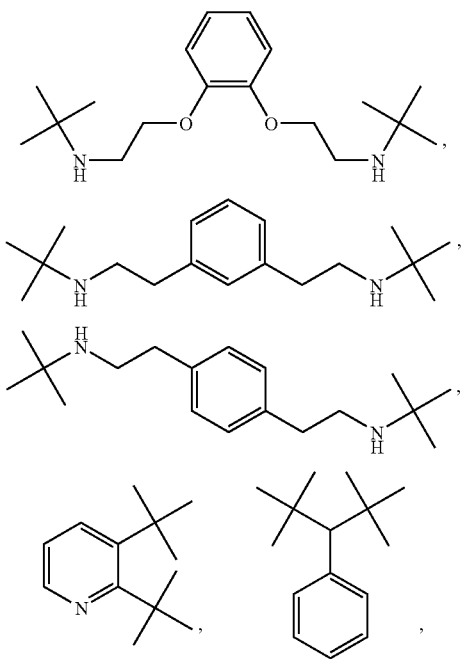

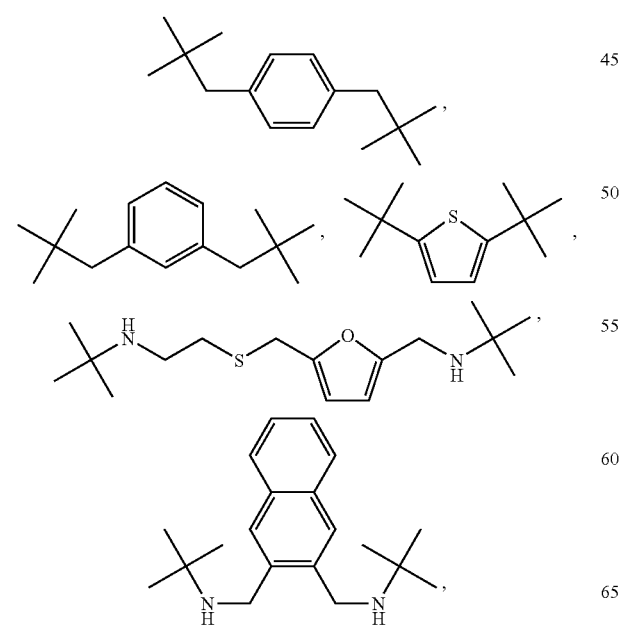

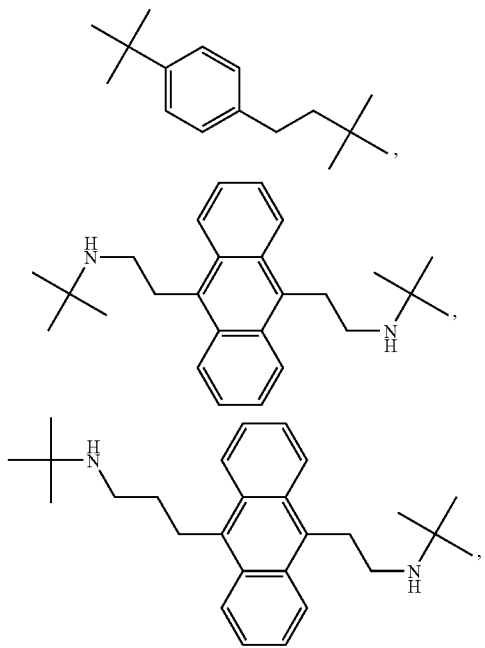

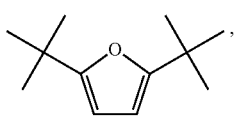
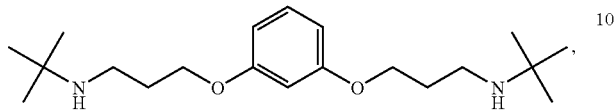
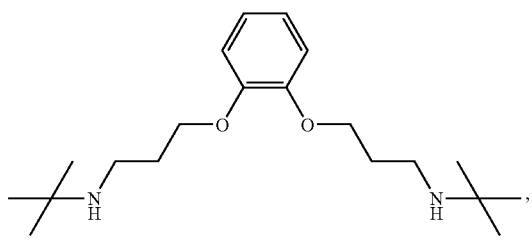
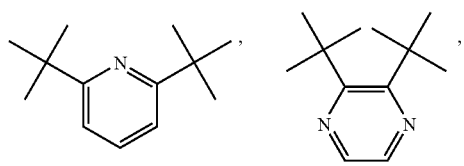
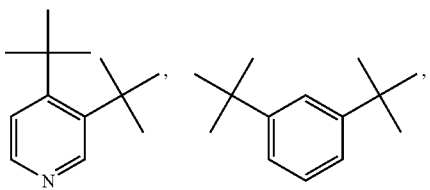
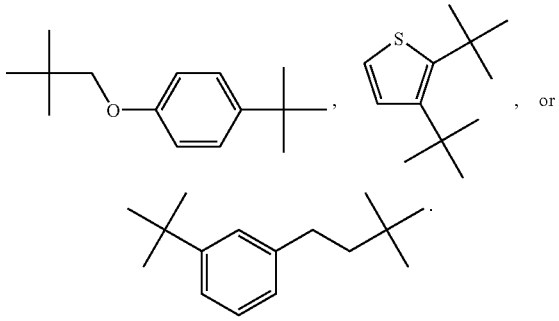
19. A pharmaceutical composition comprising a compound according to claim 18 and a pharmaceutically acceptable carrier.
* * * * *